(12) United States Patent
Fujioka et al.

(10) Patent No.: US 8,242,070 B2
(45) Date of Patent: Aug. 14, 2012

(54) METHOD FOR PRODUCING ANIONIC SURFACTANT

(75) Inventors: Toku Fujioka, Wakayama (JP); Tatsuki Matsumoto, Wakayama (JP); Hisashi Goda, Wakayama (JP)

(73) Assignee: Kao Corporation, Tokyo (JP)

( * ) Notice: Subject to any disclaimer, the term of this patent is extended or adjusted under 35 U.S.C. 154(b) by 245 days.

(21) Appl. No.: 12/442,060

(22) PCT Filed: Oct. 15, 2007

(86) PCT No.: PCT/JP2007/070495
§ 371 (c)(1),
(2), (4) Date: Mar. 19, 2009

(87) PCT Pub. No.: WO2008/047927
PCT Pub. Date: Apr. 24, 2008

(65) Prior Publication Data
US 2011/0166374 A1   Jul. 7, 2011

(30) Foreign Application Priority Data

Oct. 16, 2006  (JP) .................. 2006-281019
Dec. 8, 2006   (JP) .................. 2006-331486

(51) Int. Cl.
*C11D 17/00*  (2006.01)
(52) U.S. Cl. ......... 510/444; 510/446; 510/426; 510/495
(58) Field of Classification Search .................. None
See application file for complete search history.

(56) References Cited

U.S. PATENT DOCUMENTS

| 6,455,488 | B1 | 9/2002 | Assmann et al. | |
| 6,946,437 | B2 * | 9/2005 | Aizawa et al. | 510/446 |
| 2002/0107167 | A1 | 8/2002 | Aizawa et al. | |
| 2005/0043202 | A1 * | 2/2005 | Umehara et al. | 510/444 |

FOREIGN PATENT DOCUMENTS

| JP | 54-106428 A | 8/1979 |
| JP | 2-222498 A | 9/1990 |
| JP | 5-331496 A | 12/1993 |
| JP | 7-133498 A | 5/1995 |
| JP | 11-5999 A | 1/1999 |
| JP | 2000-63896 A | 2/2000 |
| JP | 2001-246238 A | 9/2001 |
| JP | 2002-129194 A | 5/2002 |
| JP | 2002-129197 A | 5/2002 |
| JP | 2005-68413 A | 3/2005 |
| JP | 2006-143998 A | 6/2006 |

OTHER PUBLICATIONS

English machine translation of JP-2000-63896-A dated Feb. 29, 2000.

(Continued)

*Primary Examiner* — Necholus Ogden, Jr.
(74) *Attorney, Agent, or Firm* — Birch, Stewart, Kolasch & Birch, LLP

(57) ABSTRACT

Disclosed is the method for producing an anionic surfactant powder, including removing impurities by introducing gas into a crude anionic surfactant containing water in a content of 0.01 to 5% by weight in a granulator or drier, having an agitating blade. Also disclosed is the method for producing an anionic surfactant powder, including introducing a gas along with the surface of an inner wall of a granulator or drier having an agitating blade at a reduced pressure to produce the anionic surfactant powder.

14 Claims, 2 Drawing Sheets

OTHER PUBLICATIONS

English machine translation of JP-5-331496-A dated Dec. 14, 1993.
Japanese Notice of Ground of Rejection dated Oct. 4, 2011 for Japanese Application No. 2006-281019.

Japanese Notice of Ground of Rejection dated Oct. 4, 2011 for Japanese Application No. 2006-331486.

* cited by examiner

METHOD FOR PRODUCING ANIONIC SURFACTANT

FIELD OF THE INVENTION

The present invention relates to a method for producing an anionic surfactant or a method for producing an anionic surfactant powder.

BACKGROUND OF THE INVENTION

Anionic surfactants are mixed with other surfactants or builders to be used in medical emulsifiers, cosmetic emulsifiers, and detergents including laundry detergents, kitchen detergents, and foaming agents for toothpaste.

As a method for producing an anionic surfactant powder or granule having relatively high purity, those methods have been conventionally known, including a method of spraying an anionic surfactant solution into a fluidized bed dryer to dry (U.S. Pat. No. 6,455,488), a method of drying with a rotary film evaporator to decrease a moisture content to less than 1% by weight (JP-A 11-5999), and a method of removing at least a part of solvent by irradiating a microwave (JP-A 2002-129197).

As a method for producing an anionic surfactant powder or granule, those methods have been known, including a method of spraying an aqueous slurry of alkylsulfate to dry (JP-A 54-106428), a method of forming a thin film of concentrated slurry on the inner surface of a heating wall, concentrating and drying the slurry (JP-A 2-222498, JP-A 5-331496), and a method of adding an anionic surfactant paste to a powdery raw material at a reduced pressure and simultaneously conducting drying and granulation (JP-A 2005-68413).

As a prevention against sticking of a detergent composition in production thereof by granulation, those methods have been known, including a method of adding an antisticking agent (JP-A 7-133498), a method of applying an impact force to a granulator (JP-A 2001-246238), a method of regulating a Froude number and an adding rate of a liquid raw material (JP-A 2006-143998).

SUMMARY OF THE INVENTION

The present invention (A) relates to a method for producing an anionic surfactant powder, including removing impurities by introducing gas into a crude anionic surfactant containing 0.01 to 5% by weight of water in a granulator or drier having an agitating blade.

The present invention (B) relates to a method for producing an anionic surfactant powder, including introducing a gas along the surface of an inner wall of a granulator or drier having an agitating blade at a reduced pressure to produce an anionic surfactant powder.

DETAILED DESCRIPTION OF THE INVENTION

In the method described in U.S. Pat. No. 6,455,488, the anionic surfactant solution is supplied by spraying in a fluidized bed dryer and thus is required to be kept at low viscosity. A concentration of active agent in the anionic surfactant solution is therefore required to be relatively low as about 44% by weight. To dry the water therein, or to fluidize material to be dried due to the fluidized bed dryer is used, as much as 17,000 to 20,000 $Nm^3$/h of hot air is required, and a temperature of the hot air must be very high as 170° C. The method thus has problems of requiring a huge amount of heat energy, facilitating thermal deterioration of the anionic surfactant, and emitting a huge amount of waste gas to atmosphere.

In the method described in JP-A 11-5999, hot steam or warm water is introduced into a heating jacket of the rotary film evaporator, and thereby the inner surface of a heating wall is heated. To dry to less than 1% by weight of moisture content, a temperature of the inner surface of the heating wall is required to be heated to high temperature of 110° C. or more. The method thus had a problem of difficulty in stable operation due to a possibility of hydrolysis of the anionic surfactant in contact with the inner surface of the heating wall at very high temperature while a moisture content of the anionic surfactant solution or slurry is high, and facilitation of thermal deterioration of the anionic surfactant in the case of local heating due to interruption of replacing the material to be dried on the inner surface of the heating wall.

The anionic surfactant subjected to heat history increases concerns about side reactions and hydrolysis to produce impurities and may have a problem of decreased stability in quality for a long-term storage leading unfavorable scent and taste.

Further, the method described in JP-A 2002-129197 uses microwave irradiation and thus must register a high-frequency apparatus and meet installation criteria in accordance with the Japanese Radio Law, which situation is inconvenience and lacks versatility. In addition, although heating by microwave is effective on regions containing much moisture from its principle, it has a problem of low efficiency for regions containing few moisture and substances on which microwave does not act.

The present invention provides a method for producing an anionic surfactant powder in high quality, which solves problems of those conventional methods and can remove impurities contained in the anionic surfactant effectively in a short time.

The method described in JP-A 54-106428 having the step of spraying to dry, and has a problem of need for a large drying apparatus. Further, methods described in JP-A 2-222498 and JP-A 5-331496 also have a problem of need for a large drying apparatus. In the method described in JP-A 2005-68413, which does not require a large drying apparatus, an anionic surfactant adheres to the inside of the drier and results in a decreased yield, which situation is not economical.

The method of JP-A 7-133498 uses the anti-sticking agent for adding to raw materials, and has a problem of a higher concentration of impurities in products. The method of JP-A 2001-246238 is impossible with an apparatus having a rotation shaft in the vertical direction, and has a problem of need for a sufficiently small apparatus because a granulator itself must rotate. The method of JP-A 2006-143998 shows adding a liquid raw material and treating a surface of particle with the liquid raw material. The method sufficiently solves a technical problem only when the liquid raw material is continuously added.

As described above, the conventional techniques for producing an anionic surfactant powder have problems such as a large drying apparatus and adhesion of the anionic surfactant within a drier, and have limitations in preventing adhesion such as limitation in quality and structure of an apparatus, and limitation to addition of a liquid raw material.

Therefore, there is a need for a method for producing an anionic surfactant powder in high quality, in which a drying apparatus is small and the anionic surfactant does not adhere within the drier.

The present invention provides a method for producing an anionic surfactant powder effectively, in which a drying apparatus is small and the anionic surfactant does not adhere within the drier.

According to the present invention, crude anionic surfactant dried to some extent can be uniformly heated by simultaneous heating by stirring and heating with gas regardless of its quality in sulfation or sulfonation, and neutralization/drying, and thus an anionic surfactant powder can be stably prepared in high quality from the crude anionic surfactant by effectively removing impurities therein in a short time while suppressing thermal decomposition of the anionic surfactant due to topical heating.

According to the present invention, adhesion of an anionic surfactant powder to the inner surface of a drier or granulator wall can be suppressed, and thus the anionic surfactant powder can be prepared in high yield. The present invention provides a method for producing an anionic surfactant powder in high quality, in which a drying apparatus is small, and adhesion of the anionic surfactant to the inside of the drying apparatus is few.

The present invention relates to a method for producing a highly pure anionic surfactant powder that can be preferably used in laundry detergents, kitchen detergents, foaming agents for toothpaste, powders for shampoo, emulsifiers for emulsion polymerization, medical emulsifiers, cosmetic emulsifiers, cement foaming agents, and the like.

Examples of the anionic surfactant used in the present invention include, but not limited to, alkylsulfates or alkenylsulfates, polyoxyalkylene alkyl or alkenyl ether sulfates, α-olefin sulfonates, alkylbenzenesulfonates, α-sulfofatty acid salts or esters, alkyl or alkenyl ether carbonate. Among them, from the viewpoints of foaming property and detergency performance, alkylsulfates or alkenylsulfates, and polyoxyalkylene alkyl or alkenyl ether sulfates are preferably, alkylsulfates or alkenylsulfates are more preferably, and alkylsulfates are even more preferably.

In the present invention (B), alkylsulfates, polyoxyalkylene alkyl ether sulfates, α-olefin sulfate, alkylbenzenesulfonate, and α-sulfofatty acid esters are preferably. Among them, alkylsulfates are more preferably.

Examples of a salt include alkaline metal salts, alkaline earth metal salts, ammonium salts, and alkanolamine salts. Among these salts, alkaline metal salts are preferably, and sodium salts, potassium salts, and mixtures thereof are more preferably.

Among those anionic surfactants, at least one selected from alkylsulfates or alkenylsulfates represented by the formula (I) and polyoxyalkylene alkyl or alkenyl ether sulfates represented by the formula (II) is more preferably.

(wherein, $R^1$ represents a liner or branched alkyl or alkenyl group having 8 to 24 carbon atoms; $M^1$ represents a cation; and p represents a valence number of $M^1$ and is 1 or 2.)

(wherein, $R^2$ represents a liner or branched alkyl or alkenyl group having 8 to 24 carbon atoms; A presents alkylene group having 2 to 4 carbon atoms; m' A (plural m) may be same as or different from each other; m represent an average number of moles of alkylene oxide added and is 0.05 to 20; $M^2$ represents a cation; and q represents a valence number of $M^2$ and is 1 or 2.)

In the formulae (I) and (II), the numbers of carbon of $R^1$ and $R^2$ are, from the viewpoints of caking resistance and solubility, preferably 8 to 20, and more preferably 10 to 18. A is preferably an alkylene group having 2 to 4 carbon atoms, and more preferably having 2 carbon atoms. From the viewpoints of achieving good powder characteristics and improving caking resistance, m is preferably 0.05 to 2, more preferably 0.1 to 1, and even more preferably 0.2 to 0.8. Wand $M^2$ are preferably alkaline metals such as Na and K, alkaline earth metals such as Ca and Mg, or ammonium groups unsubstituted or substituted with alkanol. Alkaline metal atoms are more preferable, and Na is even more preferable.

Example of the alkylsulfate used in the present invention (B), alkylsulfate represented by the formula (IB) is preferably:

(wherein, R represents a liner or branched alkyl or alkenyl group having 8 to 24 carbon atoms, preferably 8 to 18 carbon atoms; M represents a cation of an alkaline metal atom, an alkaline earth metal atom, an ammonium group unsubstituted or substituted with alkanol, or the like; and p represents a valence number of M and is 1 or 2.)

The alkylsulfate represented by the formula (IB) can be obtained by sulfation of a higher alcohol having 8 to 24 carbon atoms and neutralization. In sulfation, unreacted material may remain in an amount 10% or less by weight, preferably 5% or less by weight.

The alkylsulfate or alkenylsulfate represented by the formula (I) can be obtained by, for example, sulfation of an alcohol having 8 to 24 carbon atoms, preferably 8 to 20 carbon atoms (hereinafter, referred to as a higher alcohol) and neutralization. The polyoxyalkylene alkyl or alkenyl ether sulfate represented by the formula (II) can be obtained by, for example, sulfation of an alkylene oxide adduct of a higher alcohol such that an average number of moles of alkylene oxide added thereto is 0.05 to 20, preferably 0.05 to 2 and neutralization.

[Method for Producing an Anionic Surfactant Powder]

Sulfation and neutralization can be carried out by a known method. As for a sulfating agent used in sulfation, sulfur trioxide or chlorosulfonic acid is preferably. In use of a sulfur trioxide gas, it is generally used as a gas mixture diluted with an inert gas, preferably dry air or nitrogen so that a concentration of sulfur trioxide gas is 1 to 8% by volume, preferably 1.5 to 5% by volume. Examples of a neutralizer include sodium hydroxide, potassium hydroxide, and sodium carbonate.

A water content of the neutralized anionic surfactant is not specifically limited, but preferably 20 to 40% by weight from the viewpoints of fluidity and reduction of energetic load on drying. The anionic surfactant may contain a water-soluble inorganic salt, but preferably in an amount as few as possible in production of high purity anionic surfactant from the viewpoint of quality improvement. Examples of the water-soluble inorganic salt include sodium chloride, sodium sulfate decahydrate, and sodium carbonate.

The neutralized anionic surfactant is dried to produce a crude anionic surfactant. A drying method is not specifically limited. A known method can be employed. Examples of the drying method include methods using a rotary film evaporator and a spray drying device and methods of granulating and drying with a granulator or drier equipped with an agitating blade.

In the present invention, a water content of the crude anionic surfactant is, from the viewpoint of removal efficiency of impurities, 50 or less by weight, and preferably 3.0% or less by weight. From the viewpoint of productivity, the water content is 0.01% or more by weight, and preferably 0.3% or more by weight. The water content of the crude anionic surfactant can be measured by methods such as a method of weight reduction by heating, a distillation method, and the Karl Fischer method (JIS K 0068). In the present invention, the water content is measured by the Karl Fischer method (JIS K 0068).

In the present invention, the impurities contained in the anionic surfactant means petroleum ether-soluble matters. Examples of the petroleum ether-soluble matter include unsulfated alcohols in production of the anionic surfactant, alkoxylate, and a trace amount of hydrocarbon and wax produced by side reactions. A content of the petroleum ether-soluble matters is determined by dividing a weight of a petroleum ether extract by a sample weight, which extract is obtained by dissolving 100 g of sample in a mixture of 200 ml of water and ethanol, extracting with a sufficient amount of petroleum ether, distilling almost all of petroleum ether off in a water bath at 60° C., blowing the air into the extract to completely remove the petroleum ether, drying the extract in a dryer for 15 minutes at 85° C.

In the present invention, a removal rate of impurities is derived from the following calculation formula. The larger value means the faster removal rate. The "$\log_e$" means the natural logarithm.

$$\text{removal rate } [1/h] = (-\log_e(A/B))/C$$

Further, a removal ratio is led from the following calculation formula.

$$\text{removal ratio } [\%] = (1-A/B) \times 100$$

In the formula, A, B, and C refer the following means.

A: petroleum ether extract contained in a treated anionic surfactant [%]

B: petroleum ether extract contained in an untreated crude anionic surfactant [%]

C: time for treatment [h].

An average particle diameter of the crude anionic surfactant in the apparatus of the present invention is, from the viewpoints of improving fluidity in the apparatus and suppressing adhesion thereof to a wall and a filter fabric, preferably 0.01 mm or more, more preferably 0.03 mm or more, and even more preferably 0.05 mm or more. From the viewpoint of removal efficacy of impurities, the average particle diameter is preferably 3.0 mm or less, and more preferably 2.0 mm or less, and even more preferably 1.2 mm or less. In the present invention, the average particle diameter is calculated from a weight ratio of parts through each sieve using Air Jet Sieve (Hosokawa Micron Corporation model 200LS-N) under conditions of 10 g of sample weight, pressure difference between upper and under of a sieve $\Delta P = 3000$ mmH$_2$O, and 3 minutes of treatment time.

In the present invention, the crude anionic surfactant may be previously pulverized. Examples of a pulverizer used in pulverization include Atomizer (Fuji Paudal Co., Ltd.), Fits Mill (Dalton Co., Ltd.), Pulverizer (Dalton Co., Ltd.), Power Mill (Powrex Corp.), and Comill (Quadra).

The granulator or drier used in the present invention is preferably equipped with an agitating blade, a jacket for controlling an inside temperature (material temperature), and a nozzle for introducing gas. Specific examples of this preferred granulator include granulators described in JP-A 10-296064, JP-A 10-296065, and JP-B 3165700.

The granulator or drier may further be equipped with a crushing blade. The crushing blade appropriately crushes the crude anionic surfactant to increase a specific surface area, and thereby contact efficiency with the gas is increased and impurities is effectively removed.

An average particle diameter of a crushed crude anionic surfactant is, from the viewpoints of improving fluidity in the apparatus and suppressing adhesion thereof to a wall and a filter fabric, preferably 0.01 mm or more, more preferably 0.03 mm or more, and even more preferably 0.05 mm or more. From the viewpoint of removal efficacy of impurities, the average particle diameter is preferably 0.50 mm or less, and more preferably 0.30 mm or less, and even more preferably 0.20 mm or less.

Examples of the granulator or drier preferably used in the present invention include those of batch type such as Henschel mixer [Mitsui Miike Kakoki K.K.], a high-speed mixer [Fukae Powtec K.K.], a vertical granulator [Powrex Corp.], Loedige mixer [Matsuzaka Giken K.K.], a ploughshare mixer [Pacific Machinery & Engineering Co., Ltd.]. Among them, Loedige mixer [Matsuzaka Giken K. K.], a high-speed mixer [Fukae powtec K.K.], and a ploughshare mixer [Pacific Machinery & Engineering Co., Ltd.] are preferably. Examples of a continuous granulator or drier include a continuous Loedige mixer (intermediate-speed mixer: relatively long retention time) and high-speed mixers (relatively short retention time) such as CB Recycler (Loedige), Turbulizer (Hosokawa Micron Corporation), Shugi Mixer (Powrex Corp.) and Flow Jet Mixer (Funken Powtechs, Inc).

In the present invention, gas is introduced to promote the removal of impurities. An amount of introduced gas is, from the viewpoint of promoting the removal of impurities, preferably 0.2 m$^3$/Hr or more, more preferably 0.5 m$^3$/Hr or more, and even more preferably 1.0 m$^3$/Hr or more per 1 kg of anionic surfactant in the apparatus. From the viewpoint of reduction of load on equipment, the amount is preferably 20.0 m$^3$/Hr or less, more preferably 10.0 m$^3$/Hr or less, and even more preferably 5.0 m$^3$/Hr or less. A volume of a gas is at a temperature and a pressure in the apparatus.

The gas is introduced into the apparatus through a nozzle attached to the granulator or drier. Further, to increase contact efficacy with the crude anionic surfactant, the gas may be introduced so as to generate a swirling flow and/or may be introduced through a nozzle inserted in the crude anionic surfactant.

Examples of a type of gas include inert gasses such as nitrogen gas, air, and/or water vapor. Any kind of gas can exhibit similar effect particularly for removing impurities. Among them, from the viewpoints of waste gas and the scale of equipment, condensable gasses are preferable, and water vapor is more preferable. The gas may be heated to be used, and water vapor may be introduced as a superheated steam.

The crude anionic surfactant charged in the granulator or drier can be uniformly heated by using heat of the gas. A temperature of the introduced gas is preferably 20 to 120° C. From the viewpoint of use as a heat source, the temperature is more preferably 40° C. or more, and even more preferably 60° C. or more. From the viewpoint of suppressing thermal deterioration of the crude anionic surfactant, the temperature is more preferably 110° C. or less, and even more preferably 100° C. or less. Examples of other method for controlling a temperature of the anionic surfactant in the granulator or drier include methods of appropriately controlling a temperature of a jacket in the granulator and a Froude number of the agitating blade in the granulator.

Examples of a heat source of the granulator include a warm water jacket and an electric tracing. A warm water jacket is preferable. A temperature of the jacket is preferably 100° C. or less, and more preferably 90° C. or less from the viewpoint of application to a heat-sensitive material, and even more preferably 70° C. or less. From the viewpoint of use as a heat source, the temperature is preferably 30° C. or more, more preferably 40° C. or more, and even more preferably 50° C. or more.

In the present invention, an internal pressure of the granulator or drier is, from the viewpoint of increase of a volume of the gas, preferably 130 kPa or less, more preferably 101 kPa or less, even more preferably 50 kPa or less, and even more preferably 20 kPa or less. From the viewpoints of load on a vacuum pump and airtightness of the granulator, the internal pressure is preferably 0.5 kPa or more, more preferably 1.5 kPa or more, even more preferably 4.0 kPa or more, and even more preferably 5.3 kPa or more.

In the present invention, a treatment temperature of the crude anionic surfactant in the apparatus is, from the viewpoint of suppression of thermal deterioration, preferably 100° C. or less, more preferably 95° C. or less, and even more preferably 90° C. or less. From the viewpoint of improvement in removal rate of impurities, the treatment temperature is preferably 20° C. or more, more preferably 40° C. or more, and even more preferably 60° C. or more.

The highly pure anionic surfactant prepared by the present invention, from the viewpoint of effective expression of performance of an anionic surfactant itself, contains the anionic surfactant in an amount 80% or more by weight, more preferably 90% or more by weight, even more preferably 95% or more by weight and even more preferably 100% by weight.

The highly pure anionic surfactant prepared by the present invention may further contain a water-soluble inorganic salt in addition to the anionic surfactant. Examples of the water-soluble inorganic salt include sodium chloride, sodium sulfate decahydrate, and sodium carbonate. A content of the water-soluble inorganic salt in the highly pure anionic surfactant prepared by the present invention is not specifically limited, but, from the viewpoint of keeping an effective amount of the anionic surfactant high, is 5 parts or less by weight, preferably 2 parts or less by weight, more preferably 1 part or less by weight, and even more preferably 0.5 parts or less by weight, based on 100 parts of the anionic surfactants.

The highly pure anionic surfactant prepared by the present method can contain the other surfactant than the anionic surfactant. Examples of the other surfactant than the anionic surfactant include cation surfactants and nonionic surfactants.

The highly pure anionic surfactant prepared by the present method can contain other additives according to need. Examples of the other additive include alkali agents such as silicates and carbonates, divalent metal ion scavengers such as citrate and zeolite, anti-resoiling agents such as polyvinylpyrrolidone and carboxymethylcellulose, caking preventives, and antioxidants. These other additives may be used within the scope that does not interfere the object of the present invention.

In the present invention (B), an anionic surfactant powder can be prepared as follows.

In the method for producing an anionic surfactant powder of the present invention, an internal pressure of the granulator or drier must be reduced, from the viewpoint of suppression of adhere of the powder, and is preferably 0.5 to 50 kPa, more preferably 0.67 to 13.3 kPa, and from the viewpoints of load on a vacuum pump and airtightness of the granulator or drier, even more preferably 2.0 to 8.0 kPa.

A gas introduced into the granulator or drier may be any gas unless it is reactive with the anionic surfactant. Examples of the gas include air, inert gas, and water vapor. Examples of the inert gas include helium, nitrogen, argon, and carbon dioxide gas. From the viewpoint of decrease in load on a vacuum pump, condensable gasses are preferably, and water vapor is more preferably.

From the viewpoint of suppression of adhere of the powder, an amount of gas introduced into the apparatus is better as it is larger. However, from the viewpoint of load on a vacuum pump, it is preferably 0.5 to 10 m$^3$/h, and more preferably 0.5 to 5.0 m$^3$/h per 1 kg of powder in the apparatus. A volume of the gas is at a temperature and a pressure in the apparatus.

A method of introducing the gas can be any method as long as it introduces the gas along with the surface of the inner wall of the apparatus. The gas can be introduced with a blowing nozzle and the like. A position, the number, and a shape of the blowing nozzle are not specifically limited. The number of the blowing nozzle is preferably larger, because, when airflow of the gas introduced into the apparatus flows throughout the surface of the wall, the powder is suppressed from adhering.

A direction of the nozzle is preferably a direction along with the surface of the wall, particularly a circumferential direction. A swirling flow generated in the apparatus increases an effect of suppressing adhere. A direction of gas-blowing is preferably the same direction as the rotational direction of the agitating blade, because the swirling flow is easily generated.

Figure 1:
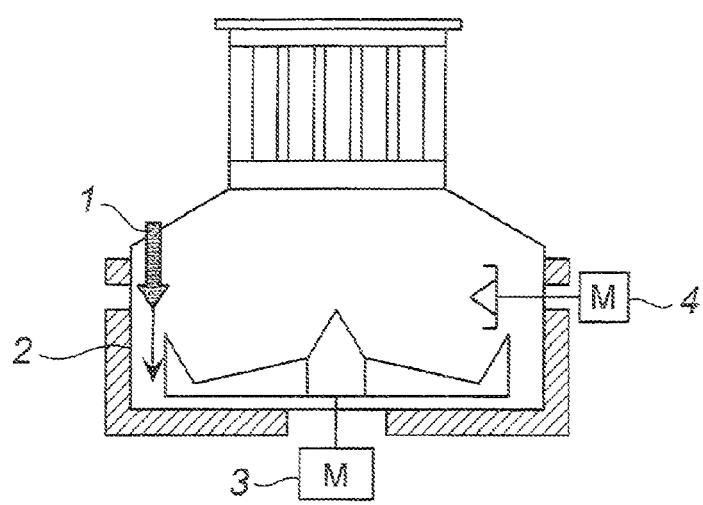
FIG. 1 shows a front view of an embodiment of an apparatus equipped with a single pipe as a blowing nozzle in a downward direction.
Figure 2:
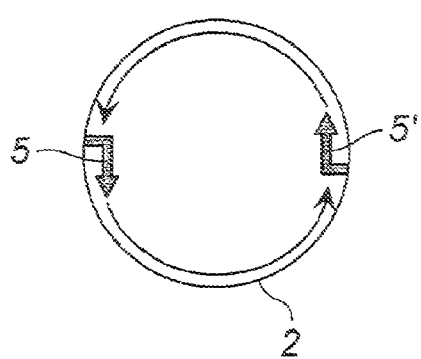
FIG. 2 shows a plan view of an embodiment of an apparatus equipped with two L-shaped pipes as blowing nozzles.
Figure 3:
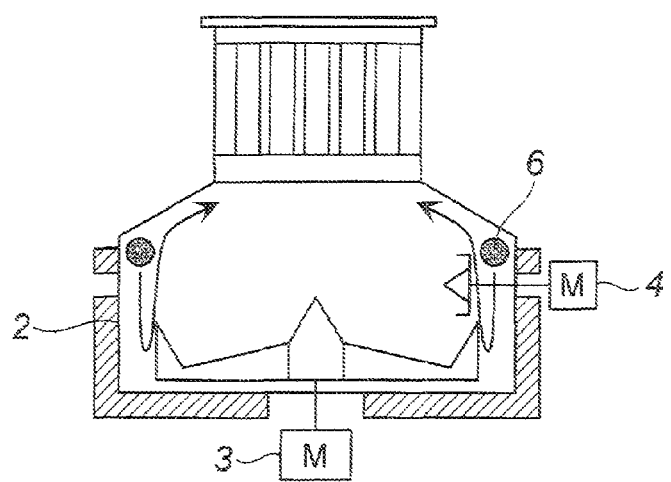
FIG. 3 shows a front view of an embodiment of an apparatus equipped with a ring sparger as a blowing nozzle.
Figure 4:
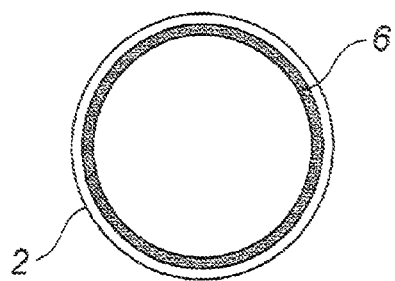
FIG. 4 shows a plan view of the apparatus in FIG. 3.
In Figures, 1 is a single pipe, 2 is the inside wall of the apparatus, 3 is an agitating blade, 4 is a crushing blade, 5 and 5' are L-shaped pipes, 6 is a ring sparger.

Embodiments of the granulator or drier equipped with a blowing nozzle used in the present invention are shown in FIGS. 1 to 4. FIG. 1 shows a front view of an embodiment of an apparatus equipped with a single pipe 1 as a blowing nozzle in a downward direction. A gas is introduced through the single pipe 1 along the surface 2 of the inner wall of the apparatus. In FIG. 1, 3 is an agitating blade, and 4 is a crushing blade. FIG. 2 shows a plan view of an embodiment of an apparatus equipped with two L-shaped pipes 5,5' as blowing nozzles. A gas is introduced through the two L-shaped pipes 5,5' along the circumferential direction on the surface 2 of the inner wall of the apparatus. In introduction, the gas is preferably blown in the same direction as the rotational direction of agitating blades, because the swirling flow is generated in the apparatus. FIG. 3 shows a front view of an embodiment of an apparatus equipped with a ring sparger 6 as a blowing nozzle. FIG. 4 is a plan view of the apparatus in FIG. 3. The ring sparger has a plurality of holes. The gas is introduced through the holes and can form an air curtain along the surface 2 of the inner wall of the apparatus. Among those blowing nozzles, the L-shaped pipe shown in FIG. 2 and the ring sparger shown in FIGS. 3 and 4 are preferable.

The granulator or drier used in the present invention is not specifically limited as long as it includes an agitating blade, but preferably further includes a crushing blade. Examples of the apparatus preferably used include Henschel mixer [Mitsui Miike Kakoki K.K.], a high-speed mixer [Fukae powtec K.K.], a vertical granulator [Powrex Corp.], Loedige mixer [Matsuzaka Giken K.K.], a ploughshare mixer [Pacific Machinery & Engineering Co., Ltd.].

In the present invention, a temperature of the anionic surfactant powder in the apparatus is preferably controlled within the range from 50 to 150° C., and more preferably from 60 to 120° C. Examples of a method for controlling the temperature include methods of appropriately controlling (1) a Froude number of the agitating blade, (2) a temperature of a jacket, and (3) a temperature of the gas introduced in the apparatus. Methods are described in detail below.

(1) A Froude Number of the Agitating Blade

In the present invention, a Froude number of the agitating blade, which is represented by the formula (II), is preferably 0.3 to 5.0, and more preferably 0.9 to 2.3.

$$Fr=V/(R \times g)^{0.5} \quad (II)$$

(wherein, Fr represents a Froude number, V represents a peripheral velocity of the agitating blade at its head [m/s], R represents a turning radius of the agitating blade [m], and g represents acceleration due to gravity [m/S$^2$].)

A Froude number 5.0 or less can reduce an amount of a powder rolling up in the apparatus and a centrifugal force to reduce an amount of a powder adhered. When a Froude number is 0.3 or more, the powder is preferably sufficiently agitated. Since the larger Froude number causes the higher temperature due to frictional heat among powder, a temperature of the powder can be controlled by controlling a Froude number.

(2) A Temperature of a Jacket

The granulator or drier used in the present invention preferably includes a jacket for controlling a temperature of a powder in the apparatus. Examples of a heat source include steam, warm water, and an electric tracing. Among them, warm water is preferable. A temperature of the jacket is preferably 115° C. or less, and from the viewpoint of application to a material sensitive to heat, more preferably 100° C. or less.

(3) A Temperature of the Gas Introduced in the Apparatus

A temperature of the gas introduced in the apparatus is not specifically limited. However, for example, when saturated water vapor is introduced, from the viewpoint of application to a material sensitive to heat, the temperature is preferably 170° C. or less (0.8 MPa), and more preferably 150° C. or less (0.5 MPa).

EXAMPLES

The following Examples illustrate embodiments of the present invention. Examples are referred to for exemplification, and not intended to limit the present invention.

In Examples, % refers % by weight unless otherwise noted.

Synthesis Example 1

Into a thin film flow-down type reactor, 2.0% by volume of sulfur trioxide gas and a higher alcohol having an alkyl group of twelve carbon atoms (molecular weight: 189) were continuously charged at 60° C. to react. Flowing amounts thereof were controlled such that a reaction molar ratio of the sulfur trioxide gas to the higher alcohol was 0.96. The sulfated product was neutralized with aqueous 23% sodium hydroxide solution, added with 30% phosphoric acid (buffering agent) to adjust pH=8, and added with water such that an effective amount of anionic surfactant was 30% to produce an aqueous sodium alkylsulfate solution (hereinafter, referred to as a sodium alkylsulfate solution 1). The sodium alkylsulfate solution 1 contained 0.9% of petroleum ether-soluble matters.

Then, the sodium alkylsulfate solution 1 was supplied to 2500 L vacuum drier [Fukae powtec K.K., model FMD-1200JE] under drying and granulating conditions of a jacket temperature: 65° C., an internal pressure of the apparatus: 4.0 kPa, a rotation number of an agitating blade: 70 r/min, and a rotation number of a crushing blade: 2000 r/min, with adjusting an amount of the sodium alkylsulfate solution 1 such that a temperature of material dried was 36.2° C., to simultaneously dry and granulate. Drying and granulating was stopped when a total amount of the solution 1 supplied was 1810 kg. A treatment was successively performed for 60 minutes under conditions of a rotation number of an agitating blade: 15 r/min, a rotation number of a crushing blade: 0 r/min, a jacket temperature: 65° C., and an internal pressure of the apparatus: 4.0 kPa to produce a powder of sodium alkylsulfate. The resultant sodium alkylsulfate powder was a crude anionic surfactant (hereinafter, referred to as a crude sodium alkylsulfate powder 1) having an average particle diameter of 1.05 mm and containing 0.99% of moisture and 2.3% of the petroleum ether-soluble.

Synthesis Example 2

An anionic surfactant [EMAL PT: Kao Corporation, average particle diameter: 0.36 mm] was milled with Atomizer (Fuji Paudal Co., Ltd., model FIIS-5) to produce a crude anionic surfactant (hereinafter, referred to as a crude sodium alkylsulfate powder 2) having an average particle diameter of 0.15 mm and containing 0.92% of moisture and 0.80% of petroleum ether-soluble matters.

Example 1

In 2500 L vacuum drier [Fukae powtec K.K., trade name: High-speed mixer model FMD-1200JE], 540 kg of crude sodium alkylsulfate powder 1 was treated with supplying superheated steam as gas at a rate of 3.2 m$^3$/Hr/kg-powder for 5 hours under conditions of a jacket temperature: 80° C., an internal pressure of the apparatus: 4.0 kPa, a rotation number of an agitating blade: 55 r/min, and a rotation number of a crushing blade: 2000 r/min to produce a highly pure sodium alkylsulfate.

Example 2

In 100 L Nauta mixer [Hosokawa Micron Corporation, model NX-1], 40 kg of crude sodium alkylsulfate powder [EMAL 10 PT: Kao Corporation, average particle diameter: 0.36 mm] was treated with supplying nitrogen gas as gas at a rate of 1.4 m$^3$/Hr/kg-powder for 5 hours under conditions of a jacket temperature: 95° C., an internal pressure of the apparatus: 5.3 kPa, and a rotation number of an agitating blade: 90 r/min to produce a highly pure sodium alkylsulfate.

Example 3

In 65 L vacuum drier [Fukae powtec K.K., trade name: High-speed mixer model FMD-65JE], 20 kg of crude sodium alkylsulfate powder 2 was treated with supplying superheated steam as gas at a rate of 9.6 m$^3$/Hr/kg-powder for 2 hours under conditions of a jacket temperature: 85° C., an internal pressure of the apparatus: 4.0 kPa, a rotation number of an agitating blade: 200 r/min, and a rotation number of a crushing blade: 0 r/min to produce a highly pure sodium alkylsulfate.

Example 4

In 65 L vacuum drier [Fukae powtec K.K., trade name: High-speed mixer model FMD-65JE], 20 kg of crude sodium alkylsulfate powder [EMAL 10P-HD: Kao Corporation, average particle diameter: 0.15 mm] was treated with supplying superheated steam as gas at a rate of 2.7 m$^3$/Hr/kg-powder for 1.5 hours under conditions of a jacket temperature: 95° C., an internal pressure of the apparatus: 10.7 kPa, a rotation number of an agitating blade: 200 r/min, and a rotation number of a crushing blade: 3000 r/min to produce a highly pure sodium alkylsulfate.

Comparative Example 1

In 65 L vacuum drier [Fukae powtec K. K., trade name: High-speed mixer model FMD-65JE], 20 kg of crude sodium alkylsulfate powder [EMAL 10P-HD: Kao Corporation, average particle diameter: 0.15 mm] was treated without gas under conditions of a jacket temperature: 95° C., an internal pressure of the apparatus: 5.3 kPa, a rotation number of an agitating blade: 200 r/min, and a rotation number of a crushing blade: 0 r/min. It took 20 hours to produce a highly pure sodium alkylsulfate.

Comparative Example 2

In 65 L vacuum drier [Fukae powtec K.K., trade name: High-speed mixer model FMD-65JE], 20 kg of crude sodium alkylsulfate powder [EMAL 10P-HD: Kao Corporation, average particle diameter: 0.15 mm] was added with 1.8 kg of water, stirred for 5 minutes under conditions of a jacket temperature: 20° C., an internal pressure of the apparatus: 101.3 kPa, a rotation number of an agitating blade: 200 r/min, and a rotation number of a crushing blade: 3000 r/min, and then treated under the same condition as in Example 4. A removal rate was decreased, compared to Example 4.

Treatment conditions and results in Examples 1 to 4 and Comparative Examples 1 to 2 are shown in Table 1.

TABLE 1

| | | Example | | | | Comparative example | |
|---|---|---|---|---|---|---|---|
| | | 1 | 2 | 3 | 4 | 1 | 2 |
| Crude anionic surfactant | | | | | | | |
| Water content | [%] | 0.99 | 1.03 | 0.92 | 0.10 | 1.20 | 8.36 |
| Average particle diameter | [mm] | 1.05 | 0.36 | 0.15 | 0.15 | 0.15 | 0.15 |
| Content of petroleum ether-soluble matters | [%] | 2.4 | 0.7 | 0.8 | 1.3 | 1.3 | 0.7 |
| Treatment condition | | | | | | | |
| Kind of gas blown | | Super-heated steam | Nitrogen gas | Super-heated steam | Super-heated steam | — | Super-heated steam |
| Amount of gas blown | [m$^3$/Hr/kg-powder] | 3.2 | 1.4 | 9.6 | 2.7 | 0 | 2.7 |
| Internal pressure of the apparatus | [kPa] | 4.0 | 5.3 | 4.0 | 10.7 | 5.3 | 10.7 |
| Temperature of anionic surfactant in the apparatus | [° C.] | 96 | 78-88 | 72 | 100 | 91 | 100 |
| Treatment time | [Hr] | 5 | 5 | 2 | 1.5 | 20 | 1.5 |
| Treatment result | | | | | | | |
| Content of petroleum ether-soluble matters | [%] | 0.11 | 0.13 | 0.05 | 0.6 | 0.3 | 0.38 |
| Removal rate of petroleum ether-soluble matters | [1/h] | 0.62 | 0.35 | 1.39 | 0.49 | 0.07 | 0.41 |
| Removal ratio of petroleum ether-soluble matters | [%] | 95 | 82 | 94 | 52 | 77 | 46 |
| Content of anionic surfactant | [%] | 99.9 | 99.1 | 99.3 | 99.3 | 99.2 | 99.3 |
| Average particle diameter of anion surfactant powder | [mm] | 0.05 | 0.4 | 0.04 | 0.09 | 0.4 | 0.10 |

The present invention (B) will be described in detail in reference with Examples 5 to 11 below.

Example 5

In 2500 L vacuum drier [Fukae powtec K.K., model FMD-1200JE] equipped with a single pipe 1 having an inner diameter of 25 mmϕ as a blowing nozzle in a downward direction shown in FIG. 1 and including an agitating blade 3 and a crushing blade 4, 543 kg of powder of sodium alkylsulfate (Emal 10P-HD, Kao Corporation, mixture of 67% by mol of those having an alkyl group of 12 carbon atoms, 28% by mol of those having an alkyl group of 14 carbon atoms, 5% by mol of those having an alkyl group of 16 carbon atoms) was treated with blowing steam along the surface 2 of the inner wall of the apparatus for 5 hours under conditions of a pressure: 5.3 kPa, a jacket temperature: 80° C., a rotation number of an agitating blade: 55 rpm, a Froude number of an agitating blade: 1.8, a rotation number of a crushing blade: 2000 rpm, a blowing amount of steam from the single pipe 1: 60 kg/h (3.7 m$^3$/h per 1 kg of powder), and a steam pressure: 0.79 MPa, to produce a powder of sodium alkylsulfate. A temperature of the powder was 106.5° C., and a recovery rate was 86.2%.

Example 6

In 2500 L vacuum drier [Fukae powtec K.K., model FMD-1200JE] equipped with two L-shaped pipes 5 and 5' having an inner diameter of 25 mmϕ as blowing nozzles shown in FIG. 2 and including an agitating blade and a crushing blade, 543 kg of powder of sodium alkylsulfate (Emal 10P-HD) was treated with blowing steam along the surface 2 of the inner wall of the apparatus in the same direction as the rotational direction of the agitating blade for 4 hours under conditions of a pressure: 5.3 kPa, a jacket temperature: 80° C., a rotation number of the agitating blade: 55 rpm, a Froude number of the agitating blade: 1.8, a rotation number of a crushing blade: 2000 rpm, a blowing amount of steam from the L-shaped pipes 5 and 5': 60 kg/h (3.6 m$^3$/h per 1 kg of powder), and a steam pressure: 0.79 MPa, to produce a powder of sodium alkylsulfate. A temperature of the powder was 96.2° C., and a recovery rate was 94.9%.

Example 7

In 2500 L vacuum drier [Fukae powtec K.K., model FMD-1200JE] equipped with a ring sparger 6 having an inner diameter of 10 mmφ and 16 holes as a blowing nozzle shown in FIGS. 3 and 4 and including an agitating blade 3 and a crushing blade 4, 543 kg of powder of sodium alkylsulfate (Emal 20P-2, Kao Corporation, an alkyl group had 12 carbon atoms) was treated with blowing steam along the surface 2 of the inner wall of the apparatus while allowing to adhere to the inside of the apparatus for 5 hours under conditions of a pressure: 5.3 kPa, a jacket temperature: 80° C., a rotation number of the agitating blade: 55 rpm, a Froude number of the agitating blade: 1.8, a rotation number of a crushing blade: 2000 rpm, a blowing amount of steam from the ring sparger 6: 20 kg/h (1.2 m$^3$/h per 1 kg of powder), and a steam pressure: 0.29 MPa, to produce a powder of sodium alkylsulfate. A temperature of the powder was 98.6° C., and a recovery rate was 100%.

Example 8

In the same 2500 L vacuum drier [Fukae powtec K.K., model FMD-12003E] equipped with two L-shaped pipes and including an agitating blade and a crushing blade as in Example 6, 543 kg of powder of the same sodium alkylsulfate as in Example 1 was treated with blowing steam along the surface of the inner wall of the apparatus in the same direction as the rotational direction of the agitating blade for 3 hours under conditions of a pressure: 5.3 kPa, a jacket temperature: 80° C., a rotation number of the agitating blade: 55 rpm, a Froude number of the agitating blade: 1.8, a rotation number of a crushing blade: 2000 rpm, a blowing amount of steam: 20 kg/h (1.2 m$^3$/h per 1 kg of powder), and a steam pressure: 0.79 MPa, to produce a powder of sodium alkylsulfate. A temperature of the powder was 96.0° C., and a recovery rate was 83.2%.

Example 9

In the same 2500 L vacuum drier [Fukae powtec K.K., model FMD-1200JE] equipped with two L-shaped pipes and including an agitating blade and a crushing blade as in Example 2, 543 kg of powder of the same sodium alkylsulfate as in Example 7 was treated with blowing steam along the surface of the inner wall of the apparatus in the same direction as the rotational direction of the agitating blade for 4 hours under conditions of a pressure: 5.3 kPa, a jacket temperature: 80° C., a rotation number of the agitating blade: 55 rpm, a Froude number of the agitating blade: 1.8, a rotation number of a crushing blade: 2000 rpm, a blowing amount of steam: 40 kg/h (2.4 m$^3$/h per 1 kg of powder), and a steam pressure: 0.29 MPa, to produce a powder of sodium alkylsulfate. A temperature of the powder was 90.7° C., and a recovery rate was 87.2%.

Example 10

In the same 2500 L vacuum drier [Fukae powtec K.K., model FMD-1200JE] equipped with two L-shaped pipes and including an agitating blade and a crushing blade as in Example 6, 543 kg of powder of the same sodium alkylsulfate as in Example 3 was treated with blowing steam along the surface of the inner wall of the apparatus in the same direction as the rotational direction of the agitating blade for 4 hours under conditions of a pressure: 5.3 kPa, a jacket temperature: 80° C., a rotation number of the agitating blade: 55 rpm, a Froude number of the agitating blade: 1.8, a rotation number of a crushing blade: 2000 rpm, a blowing amount of steam: 60 kg/h (3.5 m$^3$/h per 1 kg of powder), and a steam pressure: 0.79 MPa, to produce a powder of sodium alkylsulfate. A temperature of the powder was 92.9° C., and a recovery rate was 88.7%.

Example 11

In the same 2500 L vacuum drier [Fukae powtec K.K., model FMD-1200JE] equipped with two L-shaped pipes and including an agitating blade and a crushing blade as in Example 6, 543 kg of powder of the same sodium alkylsulfate as in Example 1 was treated with blowing steam along the surface of the inner wall of the apparatus in the same direction as the rotational direction of the agitating blade for 4.5 hours under conditions of a pressure: 5.3 kPa, a jacket temperature: 80° C., a rotation number of the agitating blade: 40 rpm, a Froude number of the agitating blade: 1.3, a rotation number of a crushing blade: 2000 rpm, a blowing amount of steam: 60 kg/h (3.6 m$^3$/h per 1 kg of powder), and a steam pressure: 0.79 MPa, to produce a powder of sodium alkylsulfate. A temperature of the powder was 99.2° C., and a recovery rate was 92.5%.

Comparative Example 3

In 2500 L vacuum drier [Fukae powtec K.K., model FMD-1200JE] including an agitating blade and a crushing blade, 543 kg of powder of the same sodium alkylsulfate as in Example 3 was treated without blowing a gas for 10 hours under conditions of a pressure: 5.3 kPa, a jacket temperature: 65° C., a rotation number of the agitating blade: 55 rpm, a Froude number of the agitating blade: 1.8, and a rotation number of a crushing blade: 2000 rpm, to produce a powder of sodium alkylsulfate. A temperature of the powder was 107.8° C., and a recovery rate was 63.7%.

Comparative Example 4

In 2500 L vacuum drier [Fukae powtec K.K., model FMD-1200JE] including an agitating blade and a crushing blade, 543 kg of powder of the same sodium alkylsulfate as in Example 1 was treated without blowing a gas for 6 hours under conditions of a pressure: 5.3 kPa, a jacket temperature: 80° C., a rotation number of the agitating blade: 55 rpm, a Froude number of the agitating blade: 1.8, and a rotation number of a crushing blade: 2000 rpm, to produce a powder of sodium alkylsulfate. A temperature of the powder was 109.5° C., and a recovery rate was 71.7%.

Treatment conditions and results in Examples 5 to 11 and Comparative Examples 3 to 4 are shown in Table 2.

TABLE 2

|  |  | Example | | | | | | | Comparative example | |
|---|---|---|---|---|---|---|---|---|---|---|
|  |  | 1 | 2 | 3 | 4 | 5 | 6 | 7 | 1 | 2 |
| Carbon number of an alkyl group in sodium alkylsulfate | | 12, 14, 16 | 12, 14, 16 | 12 | 12, 14, 16 | 12 | 12 | 12, 14, 16 | 12 | 12, 14, 16 |
| Internal pressure of the apparatus | (kPa) | 5.3 | 5.3 | 5.3 | 5.3 | 5.3 | 5.3 | 5.3 | 5.3 | 5.3 |
| Rotation number of agitating blade | (rpm) | 55 | 55 | 55 | 55 | 55 | 55 | 40 | 55 | 55 |
| Froude number of agitating blade | (—) | 1.8 | 1.8 | 1.8 | 1.8 | 1.8 | 1.8 | 1.3 | 1.8 | 1.8 |
| Rotation number of a crushing blade | (rpm) | 2000 | 2000 | 2000 | 2000 | 2000 | 2000 | 2000 | 2000 | 2000 |
| Jacket temperature | (°C.) | 80 | 80 | 80 | 80 | 80 | 80 | 80 | 65 | 80 |
| amount of steam blown | (kg/h) | 60 | 60 | 20 | 20 | 40 | 60 | 60 | 0 | 0 |
| Flowing amount of steam | (m$^3$/h · kg-powder) | 3.7 | 3.6 | 1.2 | 1.2 | 2.4 | 3.5 | 3.6 | 0 | 0 |
| Steam pressure | (MPa) | 0.79 | 0.79 | 0.29 | 0.79 | 0.29 | 0.79 | 0.79 | — | — |
| Kind of blowing nozzule | | A single pipe in a downward direction | Two L-shaped pipes | Ring sparger | Two L-shaped pipes | Two L-shaped pipes | Two L-shaped pipes | Two L-shaped pipes | — | — |
| Treatment time | (h) | 5 | 4 | 5 | 3 | 4 | 4 | 4.5 | 10 | 6 |
| Temperature of powder | (°C.) | 106.5 | 96.2 | 98.6 | 96.0 | 90.7 | 92.9 | 99.2 | 107.8 | 109.5 |
| Recovery rate | (%) | 86.2 | 94.9 | 100 | 83.2 | 87.2 | 88.7 | 92.5 | 63.7 | 71.7 |

The invention claimed is:

1. A method for producing an anionic surfactant powder, comprising introducing a gas along the surface of an inner wall of a granulator or drier, provided with an agitating blade, at a reduced pressure to remove impurities by introducing the as into a crude anionic surfactant comprising 0.01 to 5% by weight of water and to produce the anionic surfactant powder containing a reduced amount of petroleum ether-soluble matters;

wherein the gas is water vapor; and wherein the anionic surfactant is an alkylsulfate salt.

2. The method for producing an anionic surfactant powder according to claim 1, wherein the gas is introduced in the same direction as a rotational direction of the agitating blade.

3. The method for producing an anionic surfactant powder according to claim 1 or 2, wherein an amount of gas introduced is 0.5 to 10 m$^3$/h per 1 kg of the powder in the granulator or drier.

4. The method for producing an anionic surfactant powder according to claim 1, wherein an internal pressure of the granulator or drier is 0.5 to 50 kPa.

5. The method for producing an anionic surfactant powder according to claim 1, wherein the granulator or drier, provided with the agitating blade, is further provided with a crushing blade.

6. The method for producing an anionic surfactant powder according to claim 1, wherein the temperature of the anionic surfactant in the granulator or drier is 20 to 100° C.

7. The method for producing an anionic surfactant powder according to claim 1, wherein an average particle diameter of the anionic surfactant powder in the granulator or drier is 0.01 to 0.50 mm.

8. A method for recovering an alkylsulfate salt powder containing a reduced amount of petroleum ether-soluble matters, comprising introducing water vapor along the surface of an inner wall of a granulator or drier, provided with an agitating blade, at a reduced pressure into a crude alkylsulfate salt comprising 0.01 to 5% by weight of water to recover the alkylsulfate salt powder.

9. The method according to claim 8, wherein the gas is introduced in the same direction as a rotational direction of the agitating blade.

10. The method according to claim 8, wherein an amount of gas introduced is 0.5 to 10 m$^3$/h per 1 kg of the powder in the granulator or drier.

11. The method according to claim 8, wherein an internal pressure of the granulator or drier is 0.5 to 50 kPa.

12. The method according to claim 8, wherein the granulator or drier, provided with the agitating blade, is further provided with a crushing blade.

13. The method according to claim 8, wherein the temperature of the alkylsulfate salt in the granulator or drier is 20 to 100° C.

14. The method according to claim 8, wherein an average particle diameter of the alkyl sulfate salt powder in the granulator or drier is 0.01 to 0.50 mm.

* * * * *